United States Patent [19]
Krämer et al.

[11] Patent Number: 4,492,795
[45] Date of Patent: Jan. 8, 1985

[54] ALKYLCYCLOALKYL IMIDAZOLYLMETHYL KETONES AS FUNGICIDE INTERMEDIATES

[75] Inventors: Wolfgang Krämer, Wuppertal; Manfred Jautelat, Burscheid; Eckart Kranz, Wuppertal, all of Fed. Rep. of Germany

[73] Assignee: Bayer Aktiengesellschaft, Leverkusen, Fed. Rep. of Germany

[21] Appl. No.: 438,087

[22] Filed: Nov. 1, 1982

[30] Foreign Application Priority Data

Nov. 19, 1981 [DE] Fed. Rep. of Germany ....... 3145858

[51] Int. Cl.$^3$ ............................................ C07D 233/60
[52] U.S. Cl. ..................................... 548/341; 548/336
[58] Field of Search ......................................... 548/341

[56] References Cited

U.S. PATENT DOCUMENTS 4,073,925  2/1978  Balasubramanyan ........... 548/341 X
4,291,044  9/1981  Jäger et al. ..................... 548/341 X
4,317,830  3/1982  Thorogood ..................... 424/273 R
4,396,771  8/1983  Thorogood ........................ 548/341

FOREIGN PATENT DOCUMENTS 2333354  1/1975  Fed. Rep. of Germany ...... 548/341

OTHER PUBLICATIONS

Larcheveque, M. et al., *Journal of Organometallic Chemistry*, 57 (1973), pp. 33–35.

Primary Examiner—Richard A. Schwartz
Attorney, Agent, or Firm—Sprung, Horn, Kramer & Woods

[57] ABSTRACT

New alkylcycloalkyl imidazolylmethyl ketones of the general formula

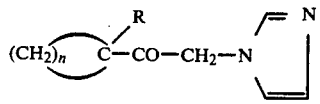

in which
  R represents an alkyl group and
  n is 3, 4, 5, 6 or 7, are produced as described and find use as intermediate products for the preparation of imidazolyl-vinyl-dithioacetals, which possess fungicidal properties.

3 Claims, No Drawings

ALKYLCYCLOALKYL IMIDAZOLYLMETHYL KETONES AS FUNGICIDE INTERMEDIATES

The present invention relates to certain new alkylcycloalkyl imidazolymethyl ketones, to an unobvious process for their production, and to their use as intermediate products for the synthesis of imidazolyl-vinyl-dithioacetals, which possess fungicidal properties.

It has already been disclosed that certain triazolyl-alkenones possess good fungicidal properties (see U.S. Pat. No. 4,331,675.) Thus, for example, 4,4-dimethyl-1-(napth-2-yl)-2-(1,2,4-triazol-1-yl)-pent-1-en-3-one can be empolyed for combating fungi. However, the action of this compound is not always entirely satisfactory, particularly when low amounts and concentrations are used.

The present invention now provides, as new compounds, the alkylcycloalkyl imidazolylmethyl ketones of the general formula

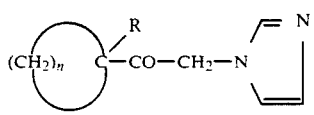

(I)

in which
R represents an alkyl group and
n is 3,4,5, 6 or 7.

According to the present invention we further provide a process for the production of alkylcycloalkyl imidazolylmethyl ketones of the present invention, characterized in that an alkylcycloalkyl halogenomethyl ketone of the general formula

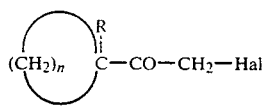

(II)

in which
R and n have the meanings given above and
Hal represents a chlorine or bromine atom, is reacted with imidazole of the formula

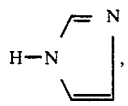

(III)

in the presence of a diluent and in the presence of an acid-binding agent.

The new alkylcycloalkyl imidazolylmethyl ketones are interesting intermediate products for the preparation of active compounds for plant protection. Thus, the substances of the formula (I) are suitable, for example, as starting materials for the synthesis of imidazolyl-vinyl-dithioacetals, which possess very good fungicidal activity.

Surprisingly, the imidazolyl-vinyl-dithioacetals, which can be prepared from the alkylcycloalkyl imidazolylmethyl ketones according to the invention, of the formula (I), by successive reaction with carbon disulphide and an alkylating agent, have a superior fungicidal activity compared with the compound 4,4-dimethyl-1-(naphth-2-yl)-2-(1,2,4-triazol-1-yl)-pent-1-en-3-one which is known from the prior art.

Preferred compounds of formula (I) according to the invention are those in which
R represents a straight-chain or branched alkyl group having 1 to 6 carbon atoms and
n has the meaning given above.

Those compounds of the formula (I), in which R represents a methyl or ethyl group, are particularly preferred.

In addition to the compounds mentioned in the examples hereinbelow, the following compounds of the formula (I) may be mentioned individually:

TABLE 1

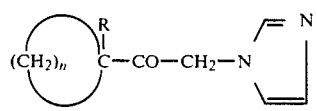

| R | n |
|---|---|
| CH$_3$ | 3 |
| CH$_3$ | 4 |
| CH$_3$ | 5 |
| CH$_3$ | 6 |
| CH$_3$ | 7 |
| C$_2$H$_5$ | 3 |
| C$_2$H$_5$ | 4 |
| C$_2$H$_5$ | 5 |
| C$_2$H$_5$ | 6 |
| C$_2$H$_5$ | 7 |

If, for example, 1-chloroacetyl-1-ethylcyclopentane and imidazole are used as starting materials, the course of the reaction in the process according to the invention can be represented by the following equation:

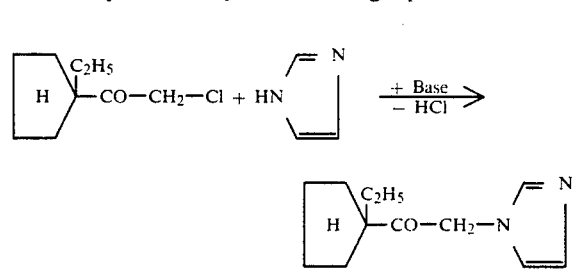

Preferred alkylcycloalkyl halogenomethyl ketones of formula (II) required as starting materials for carrying out the process according to the invention are those in which R has the meaning given for this radical in connection with the description of the preferred and particularly preferred compounds according to the invention, of the formula (I), and Hal and n have the meanings given above.

The alkylcycloalkyl halogenomethyl ketones of the formula (II) were hitherto unknown. However, they can be prepared in a simple manner by processes which are known in principle. Thus, an alkylcycloalkyl halogenomethyl ketone of the formula (II) is obtained by reacting a 1,1-dichloroalkene of the general formula (IV)

(CH$_2$)$_n$ C—CH=CCl$_2$ in which R and n have the meanings given above, with a phenolate of the general formula

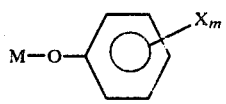  (V)

in which
M represents one equivalent of an alkali metal ion or an alkaline earth metal ion, especially of a sodium ion or potassium ion,
X represents a halogen atom, or an alkyl or alkoxy group, each having 1 to 3 carbon atoms, or a phenyl group, and
m is 0, 1 or 2,
in the presence of an inert organic solvent (such as dimethylformamide) at a temperature between 100° and 220° C., if appropriate under elevated pressure, and hydrolyzing the resulting phenyl ether of the general formula

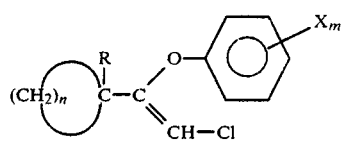  (VI)

in which R, X, m and n have the meanings given above, in a customary manner with a mineral acid (such as sulphuric acid or hydrochloric acid) and/or with an organic acid (such as formic acid), at 40° to 100° C.

The preparation of 1,1-dichloroalkenes of the formula (IV) is known. It is effected by the addition reaction of alkyl halides with vinylidene chloride in the presence of acidic catalysts (in this context, see J. Amer. Chem. Soc. 74, 2885 (1952)), hydrogen halide being split off at the same time.

The phenolates of the formula (V) are generally known compounds of organic chemistry.

The alkylcycloalkyl halogenomethyl ketones of the formula (II) can also be obtained by reacting an alkylcycloalkyl methylketone of the general formula

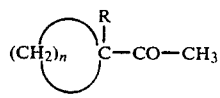  (VII)

in which R and n have the meanings given above, in the customary manner with chlorine or bromine, in the presence of an inert organic solvent (such as a chlorinated or unchlorinated hydrocarbon), at room temperature, or with a customary chlorinating agent (such as sulphuryl chloride), at 20° to 60° C.

The alkylcycloalkyl methyl ketones of the formula (VII) are obtained by reacting the corresponding nitrile of the general formula

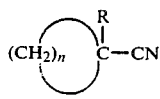  (VIII)

in which R and n have the meanings given above, in the customary manner with an organometallic compound, (such as, especially, methyl magnesium bromide) in the presence of a diluent (such as an anhydrous ether), at a temperature between 0° and 80° C.

Nitriles of the formula (VIII) are known (see Journal of Organometallic Chemistry 57, C 33–35 (1973)), and they can be obtained according to the process given in this publication.

Inert organic solvents are suitable diluents for the process according to the invention. These preferably include, as preferences, ketones (such as acetone, methyl ethyl ketone and methyl butyl ketone), alcohols (such as ethanol, isopropanol and butanol), aromatic hydrocarbons (such as benzene and toluene), formamides and sulphoxides (such as dimethylformamide and dimethylsulphoxide), and nitriles (such as acetonitrile).

The process according to the invention is carried out in the presence of an acid-binding agent. It is possible to add any of the customarily usable inorganic or organic acid-binding agents, such as alkali metal carbonates (for example sodium carbonate, potassium carbonate and sodium bicarbonate), alkali metal hydroxides and alkaline earth metal hydroxides (for example potassium hydroxide and calcium hydroxide), or lower tertiary alkylamines, cycloalkylamines or aralkylamines (for example triethylamine, N,N-dimethylmethycyclohexylamine, dicyclohexylamine and N,N-dimethybenzylamine, and furthermore pyridine and diazabicyclooctane).

Preferably, an appropriate excess of imidazole is used.

In the process according to the invention, the reaction temperatures can be varied within a relatively wide range. In general, the reaction is carried out at a temperature between 0° and 120° C., preferably between 20° and 90° C. Advantageously, the reaction is carried out at the boiling point of the particular solvent.

In carrying out the process according to the invention, 1 to 4 mols of imidazole and 1 to 4 mols of the acid-binding agent are preferably employed per mol of the compounds of the formula (II). To isolate the compound of the formula (I), the solvent is distilled off and the residue is worked up in the customary manner.

The alkylcycloalkyl imidazolylmethyl ketones according to the invention, of the formula (I), are suitable intermediate products for the synthesis of imidazolyl-vinyl-dithioacetals, which possess fungicidal activity.

Such imidazolyl-vinyl-dithioacetals of the general formula

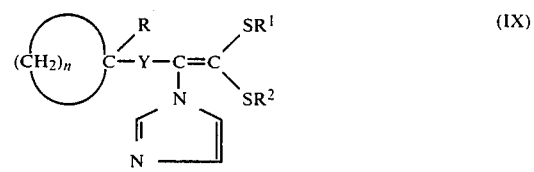  (IX)

in which
R and n have the meanings given above,
$R^1$ and $R^2$ are identical and represent an alkyl, alkenyl, alkinyl, optionally substituted benzyl or trialkylsilyl group, or
$R^1$ and $R^2$ together represent an alkylene chain, a dialkylsilyl bridge, or the —CH=CH—group, and
Y represents a keto group or a CH(OH) group, can be prepared by a process in which carbon disulphide is first added to an alkylcycloalkyl imidazolylmethyl ketone of the general formula

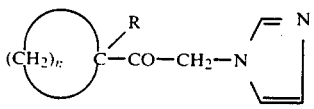 (I)

in which R and n have the meanings given above, in the presence of a base and in the presence of a diluent, and the product is then reacted again (α) with a compound of the general formula

 (X)

in which
Hal' represents a halogen atom and
R³ represents an alkyl, alkenyl, alkinyl, optionally substituted benzyl or trialkylsilyl group,
or (β) with dimethyl sulphate of the formula (CH₃)₂SO₄      (XI)

or (γ) with a dihalide of the general formula
 (Xii)

in which
Hal" represents a halogen atom and
R⁴ represents a methylene chain having one or more members, a dialkylsilyl bridge, or a —CH=CH— group,
in the presence of the same diluent; and, if a compound of formula (IX) is required in which Y represents a CH(OH) group, the resulting keto derivative of the formula

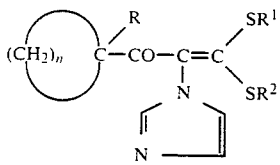 (IXa)

in which R, R¹, R² and n have the meanings given above, is reduced in the generally customary manner.

Preferred imidazolyl-vinyl-dithioacetal of formula (IX) which can be prepared from the substances according to the invention are those in which Y and n have the meanings given above, R has the meaning which has already been mentioned for this radical in connection with the description of the preferred and particularly preferred compounds according to the invention, of the formula (I), and R¹ and R² preferably represent the same radical which is a straight-chain or branched alkyl group having 1 to 4 carbon atoms, is a straight-chain or branched alkenyl and alkinyl group, each having 2 to 6 carbon atoms, is an optionally substituted benzyl group, substituent(s) on the phenyl ring of the benzyl group being selected from halogen, alkyl, alkoxy and alkylthio, each having 1 to 4 carbon atoms; halogenoalkyl, halogenoalkoxy and halogenoalkylthio, each having 1 to 2 carbon atoms and up to 5 identical or different halogen atoms (such as, especially, fluorine atoms and chlorine atoms) and phenoxy and phenyl optionally substituted by halogen and/or by alkyl having 1 to 2 carbon atoms; or is a trialkylsilyl group having 1 to 4 carbon atoms in each alkyl part or R¹ and R² together represent an alkylene chain having 1 to 4 carbon atoms, a dialkylsilyl bridge having 1 to 4 carbon atoms in each alkyl part, or the —CH=CH— group.

Preferred compounds of formulae (X) and (XII) to be used as reactants in the preparation of imidazolyl-vinyl-dithioacetals of formula (IX) are those in which; in the case of compounds of formula (X) Hal' represents a chlorine or bromine atom, and R³ has the meanings which have already been mentioned for R' in the description of the preferred compounds of the formula (IX); and, in the case of compounds of formula (XII), Hal" represents a chlorine or bromine atom, and R⁴ has the meanings which have already been mentioned for the formation of substituents by R¹ and R² together, in the description of the preferred compounds of the formula (IX).

The compounds of the formulae (X), (XI) and (XII) are generally known compounds of organic chemistry.

Suitable diluents for the process for the preparation of the keto derivatives of the formula (IXa) are organic solvents which are inert under the reaction conditions. These include, as preferences, ethers (such as tetrahydrofuran or dioxane), alcohols (such as methanol, ethanol or isopropanol), amides (such as dimethylformamide or dimethylacetamide) and also dimethylsulphoxide, hexamethylphosphoric acid triamide or sulpholane (tetrahydrothiophene-1,1-dioxide).

The process for the preparation of the keto derivatives of the formula (IXa) is carried out in the presence of a base. Such bases include, as preferences, alkali metal hydroxides and alcoholates (such as sodium and potassium hydroxide or sodium and potassium methylate, ethylate and tert.-butylate) and alkali metal hydrides and amides (such as sodium hydride, sodium amide or lithium isopropylamide, and butyl-lithium).

In carrying out the process for the preparation of the keto derivatives of the formula (IXa), the reaction temperatures can be varied within a relatively wide range. In general, the reaction is carried out at a temperature between 0° and 80° C., preferably between 0° and 60° C.

In carrying out the process for the preparation of the keto derivatives of the formula (IXa), 1 to 1.1 mols of carbon disulphide and 2 mols of base and 2 mols of a compound of the formula (XII) are preferably employed per mol of alkylcycloalkyl imidazolylmethyl ketone. Preferably, in this process, the ketone of the formula (I) is initially introduced. First, half the amount of carbon disulphide and base is added, then the remaining amount of carbon disulphide and base is added, and finally the particular reactant of the formula (X), (XI) or (XII) is added. The isolation of the compound of the formula (IXa) is effected in the customary manner.

If the reduction of the keto derivative of the formula (IXa) is carried out using aluminum isopropylate, preferred diluents for this reaction are alcohols (such as isopropanol), or inert hydrocarbons (such as benzene). In this case also, the reaction temperatures can be varied within a relatively wide range; in general, the reaction is carried out at a temperature between 20° and 120° C., preferably between 50° and 100° C. To carry out the reaction, about 1 to 2 mols of aluminum isopropylate are employed per mol of a ketone of the formula (IXa). To isolate the reduced compounds of the formula (IV), the excess solvent is removed by distillation in vacuo, and the aluminum compound formed is decomposed with dilute sulphuric acid or sodium hydroxide solution. Further working-up is effected in the customary manner. The imidazolyl-vinyl-dithioacetals of the formula (IX) which can be prepared from the substances according to the invention, of the formula (I), possess very good fungicidal properties.

Preparative Examples

Example 1

(a)

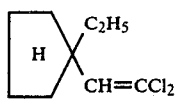
(IV-1)

10 g of anhydrous aluminum chloride were added to 291 g (3 mols) of 1,1-dichloroethene at −20° C., and thereafter 133 g (1 mol) of 1-ethyl-cyclopentyl chloride (Chem. Abstr. 42, 6238 (1948)) were added dropwise at 0° to 10° C. The reaction solution was allowed to warm up to 20° C., a further 5 g of aluminum chloride was added, and the mixture was stirred for a further 2 hours at 20° C. The mixture was poured on to ice, and was worked up with methylene chloride and dilute hydrochloric acid. 158 g (82% of theory) of 1-(2,2-dichlorovinyl)-1-ethyl-cyclopentane of boiling point 45° to 50° C./0.1 mm Hg were obtained by fractional distillation of the organic phase after the latter had been dried over sodium sulphate.

(b)

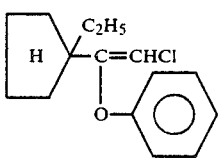
(VI-1)

140 g (4.2 mol) of sodium phenolate in 500 ml of N-methylpyrrolidone were heated to 200° C. 116 g (0.6 mol) of 1-(2,2-dichlorovinyl)-1-ethyl-cyclopentane were added dropwise so slowly that the reaction temperature did not fall below 195° C. The mixture was then stirred for a further hour at 210° C. After the mixture had cooled, it was diluted with methylene chloride and extracted several times by shaking with 2 N sodium hydroxide solution. The organic phase, which had been dried over sodium sulphate, was concentrated in vacuo, and the residue was fractionated. 132 g (88% of theory) of 1-chloro-2-(1-ethylcyclopentyl)-2-phenoxyethylene of boiling point 115° to 125° C./0.1 mm Hg were obtained.

(c)

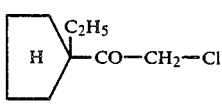
(II-1)

125.3 g (0.5 mol) of 1-chloro-2-(1-ethylcyclopentyl)-2-phenoxyethylene in 500 ml of formic acid and 50 ml of concentrated hydrochloric acid were heated at 80° C. for 2 hours. The mixture was then diluted with methylene chloride and ice, and was extracted three times by shaking with 2 N sodium hydroxide solution. After the methylene chloride phase had been dried over sodium sulphate, the solvent was evaporated off in vacuo in a rotary evaporator. The residue was distilled in vacuo.

72 g (82.6% of theory) of 1-chloroacetyl-1-ethylcyclopentane of refractive index $n_D^{20}=1.484$ were obtained.

(d)

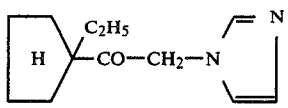
(1)

100 g (0.57 mol) of 1-chloro-acetyl-1-ethylcyclopentane and 137 g of imidazole in 1,000 ml of acetonitrile were heated under reflux for 48 hours. Thereafter, the reaction mixture was allowed to cool and was concentrated. The residue was taken up in 1,000 ml of water, and the solution was extracted by shaking with twice 500 ml of methylene chloride. The combined organic phases were washed with three times 200 ml of water, dried over sodium sulphate and concentrated. 95 g (76% of theory) of 1-ethylcyclopentyl (imidazol-1-yl)-methyl ketone in the form of a viscous oil were obtained.

The intermediates of the formula

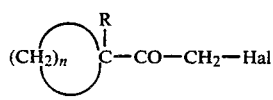
(II)

which are listed in Table 2 were obtained according to Example 1 a, b and c and according to the processes given:

TABLE 2

| Inter. No. | n | R | Hal | Physical constants b.p. (°C.)/mbar |
|---|---|---|---|---|
| (II-2) | 5 | CH$_3$ | Cl | 125–130/18 |
| (II-3) | 4 | C$_4$H$_9$ | Cl | 82–88/0.1 |
| (II-4) | 6 | CH$_3$ | Cl | 75–78/0.1 |
| (II-5) | 7 | CH$_3$ | Cl | 92–96/0.03 |

The compounds of the formula

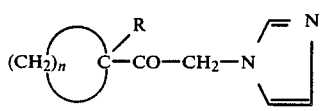
(I)

which are listed in Table 3 were obtained in an analogous manner and according to the process according to the invention:

TABLE 3

| Compound No. | n | R | Melting point (°C.) |
|---|---|---|---|
| 2 | 5 | CH$_3$ | 75–76 |

Preparation of subsequent products

The conversion of the novel compounds according to the instant invention to fungicidal active imidazol-vinyl-dithioacetals of the general formula (IX) with excellent fungicidal activity especially against powdery mildew is described in detail in German patent application No. P 31 45 890.4, filed Nov. 19, 1981, the disclosure of which is incorporated herein by reference.

The following examples are given:

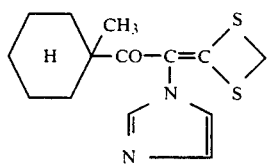 (IX-1)

27 g (0.13 mol) 1-methylcyclohexyl-(imidazol-1-yl-methyl) ketone are dissolved in 100 ml of dimethylsulfoxide and 5.2 g (0.13 ml) of sodium hydroxide are added. At 20° C. 5.32 g (0.07 mol) of carbon disulfide are added dropwise and subsequently another portion of 5.2 g (0.13 mol) of sodium hydroxide and further 5.32 g (0.07 mol) of carbon disulfide. After stirring during 20 minutes at 20° C. (cooling with ice) 28 g (0.15 mol) of dibromoethane are added. The exothermic reaction is maintained at 30° to 35° C. After stirring during 3 hours at 30° C. the reaction mixture is given in water and the cristalline mass filtered off with suction. For purification the raw material is dissolved in acetic acid ethyl ester and subjected to chromatography using a siliceous-column. There are obtained 26.5 g (69.3% of theory) of the compound of formula (IX-1) with a melting point of 184°-185° C.

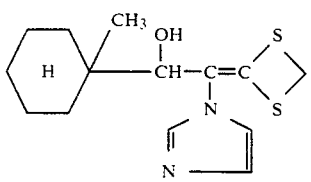 (IX-2)

8 g (28 mmols) of compound (XI-1) are dissolved in 100 ml of methanol and with stirring at 20° C. 13 g (30 mmols) of sodiumborohydride are added in portions. After 30 minutes stirring the solution is concentrated in vacuo, the residue taken up with methylenechloride/water, the organic phase separated and concentrated in vacuo. For purification the residue is subjected to chromatography in acetic acid ethyl ester using a siliceous column. There are obtained 5.6 g (70% of theory) of the compound of formula (IX-2) with a melting point of 138°-140° C.

It will be appreciated that the instant specification and examples are set forth by way of illustration and not limitation, and that various modifications and changes may be made without departing from the spirit of the present invention.

We claim:

1. An alkylcycloalkyl imidazolylmethyl ketone of the formula

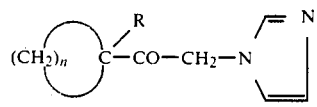

in which

R is an alkyl group having 1 to 6 carbon atoms, and n is 3, 4, 5, 6 or 7.

2. A compound according to claim 1, wherein such compound is 1-ethylcyclopentyl (imidazol-1-yl)-methyl ketone of the formula

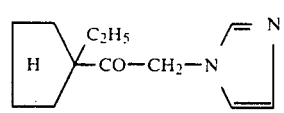

3. A compound according to claim 1, wherein such compound is 1-methylcyclohexyl (imidazol-1-yl)-methyl ketone of the formula

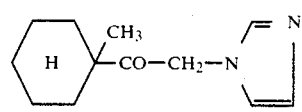

* * * * *